United States Patent
Schepis et al.

(10) Patent No.: US 12,396,708 B2
(45) Date of Patent: Aug. 26, 2025

(54) METHOD FOR DETERMINING AN INDEX FOR ASSESSING A CARDIAC FUNCTION OF A SUBJECT

(71) Applicant: ECHOSENS, Paris (FR)

(72) Inventors: Filippo Schepis, Modena (IT); Laurent Sandrin, Bourg-la-Reine (FR)

(73) Assignee: ECHOSENS SA, Paris (FR)

( * ) Notice: Subject to any disclaimer, the term of this patent is extended or adjusted under 35 U.S.C. 154(b) by 53 days.

(21) Appl. No.: 18/406,721

(22) Filed: Jan. 8, 2024

(65) Prior Publication Data

US 2025/0221690 A1  Jul. 10, 2025

(51) Int. Cl.
*A61B 8/00* (2006.01)
*A61B 8/08* (2006.01)

(52) U.S. Cl.
CPC .......... *A61B 8/5223* (2013.01); *A61B 8/0883* (2013.01); *A61B 8/461* (2013.01); *A61B 8/467* (2013.01); *A61B 8/485* (2013.01)

(58) Field of Classification Search
CPC ..... A61B 8/5223; A61B 8/0883; A61B 8/461; A61B 8/467; A61B 8/485
See application file for complete search history.

(56) References Cited

U.S. PATENT DOCUMENTS

| | | | |
|---|---|---|---|
| 2021/0057101 A1* | 2/2021 | deSa | G08B 7/06 |
| 2022/0047678 A1 | 2/2022 | Djedjos et al. | |
| 2022/0192640 A1* | 6/2022 | Vignon | A61B 8/485 |
| 2023/0107003 A1 | 4/2023 | Roh et al. | |
| 2023/0218622 A1* | 7/2023 | Goldberg | A61K 31/519 514/262.1 |
| 2024/0225606 A1* | 7/2024 | Sandrin | A61B 8/5223 |
| 2024/0382177 A1* | 11/2024 | Sandrin | A61B 8/543 |

OTHER PUBLICATIONS

Extended European Search Report as issued in European Patent Application No. 24305031.7, dated Mar. 7, 2024.

(Continued)

*Primary Examiner* — Bo Joseph Peng

(74) *Attorney, Agent, or Firm* — Pillsbury Winthrop Shaw Pittman LLP

(57) ABSTRACT

A method for determining an index for assessing a cardiac function of a subject, includes performing, by elastography, first and second liver stiffness measurements to obtain first and second values of a liver stiffness parameter of the subject, the first and second values being associated with first and second times; determining, by a processing circuit, the index of the cardiac function based on the first and second values, and outputting, via a graphical user interface of a device, the determined index of the cardiac function of the subject. The first value corresponds to a value of the liver stiffness parameter before or immediately after performing a predetermined cardiac stimulation that modifies a cardiovascular system of the subject and the second value corresponds to a value of the liver stiffness parameter obtained after performing the first liver stiffness measurement.

20 Claims, 5 Drawing Sheets

(56) References Cited

OTHER PUBLICATIONS

Taneja, S., et al., "Assessment of Liver Fibrosis by Transient Elastography Should Be Done After Hemodialysis in End Stage Renal Disease Patients with Liver Disease," Digestive Diseases and Sciences, Springer vol. 62, No. 11, Sep. 2017, pp. 3186-3192, XP036344312.

Anders, M et al., "Rapid MR elastography of the liver for subsecond stiffness sampling," International Society for Magnetic Resonance in Medicine, Aug. 2023, pp. 312-324.

Millonig, G., et al., "Liver stiffness is directly influenced by central venous pressure," Journal of Hepatology, vol. 52, No. 2, Feb. 2010, pp. 206-210.

Dhillon, J. K., et al., "Use of liver stiffness measurements in acute decompensated heart failure: new applications of a non-invasive technique," ESC Heart Failure, Jul. 12, 2022, 8 pages.

Kobalava, Z., et al., "Prognostic Value of Admission-to-Discharge Change in Integral Congestion Assessment for Predicting Adverse Outcomes in Patients with Decompensated Heart Failure," Archives of Razi Institute, vol. 77, No. 3, Jun. 2022, pp. 1049-1058.

Byenfeldt, M., et al., "Influence of Probe Pressure on Ultrasound-Based Shear Wave Elastography of the Liver Using Comb-Push 2-D Technology," Ultrasound in Medicine and Biology, vol. 45, Issue 2, (Year: 2018), pp. 411-428.

\* cited by examiner

METHOD FOR DETERMINING AN INDEX FOR ASSESSING A CARDIAC FUNCTION OF A SUBJECT

FIELD

The present invention relates to the field of cardiac evaluation. More specifically, the invention relates to determining an index for assessing a cardiac function of a subject.

BACKGROUND

The main role of the heart is to distribute oxygenated blood and nutrients to the organs. Cardiac function of a subject thus represents the ability of the heart to satisfy the metabolic demands of the body.

Heart failure occurs when the heart cannot pump enough blood through the artery to meet the metabolic organs' needs and cannot receive all the amount of venous blood that returns to the heart for oxygenation and purification. Therefore, the primary hemodynamic manifestation of heart failure is the rise in blood volume and pressure in the heart chambers, lung vessels, central veins, and peripheral veins and organs (called "congestion").

The gold standard method for assessing cardiac function is the right heart catheterization. This procedure is performed by puncturing a femoral, subclavian, internal jugular or antecubital vein. A probe is inserted into the right atrium, then through the tricuspid valve, into the right ventricle and finally into the pulmonary artery crossing the pulmonary valve. The right heart catheterization allows the pressure in the right heart chambers (e.g., right ventricular pressure or right atrium pressure) and in the pulmonary arteries to be measured with high accuracy. However, this procedure is invasive and requires a high level of expertise from the operator performing it.

There is therefore a need to develop reliable and non-invasive techniques for assessing the cardiac function in individuals, for example with risk factors or suspected or diagnosed cardiac disease.

SUMMARY

An aspect of the invention relates to determining an index (or score or cardiac function index or cardiac function index) for assessing the cardiac function of a subject based on at least two measured values of liver stiffness, which are measured before and after a cardiac challenge or a predetermined cardiac stimulation. Depending on the type of predetermined challenge or stimulation, the measurements of the two liver stiffness values can be separated from each other by a relatively short time interval, of the order of a few seconds or a few minutes, or even a few hours. For some stimulations, the time interval can even be within 1 hour, or even 30 minutes, or even a few minutes (for example within 15 minutes). In the context of the invention, the longest time interval is within 6 hours.

In the context of various aspects of the present invention, the predetermined cardiac stimulation is typically at least one of the following:
 a change of position of the subject;
 a physical activity of the subject; and
 the injection of a substance to the subject.

It is well known that there is a link between the heart and the liver. The liver, renowned for its high metabolic activity, receives approximately 25% of the cardiac output. Venous drainage from the liver occurs via the hepatic veins and the inferior vena cava, both of which lack valves. This characteristic leads to the direct transmission of filling pressures of the right heart backwards to the liver. For example, acute decompensated heart failure (ADHF) increase pressure in the right atrium, also known as central venous pressure (CVP), leading to hepatic congestion, and this relationship has prognostic significance.

In the article "Liver stiffness is directly influenced by central venous pressure" of Millonig et al., published in Journal of Hepatology, vol. 52, no 2, February 2010, p. 206-210, the authors showed a correlation between Liver Stiffness Measurement (LSM) and CVP in the context of ADHF.

In the article "Use of liver stiffness measurements in acute decompensated heart failure: new applications of a non-invasive technique" of Dhillon et al., published in ESC Heart Failure, 12 Jul. 2022, the authors reported that elevated LSM can serve as an independent predictor of increased cardiac events, all-cause mortality, and worse post-operative outcome after both ADHF exacerbation and left ventricular assist device (LVAD) placement. This article also mentions several studies which convergently concluded that there was a significant reduction in LSM after diuresis for patients admitted for ADHF.

In the article "Prognostic Value of Admission-to-Discharge Change in Integral Congestion Assessment for Predicting Adverse Outcomes in Patients with Decompensated Heart Failure" of Kobalava et al., published in Archives of Razi Institute, June 2022, the authors studied whether LSM variation between admission and discharge in subjects hospitalized for decompensated heart failure had a predictive value for the occurrence of adverse cardiac events in these subjects during the year following discharge. To do this, they determined the variation of the LSM between admission at the hospital and discharge from the hospital (the two measurements therefore being typically spaced by several days or several weeks). They compared the LSM variation between patients with adverse events and patients without adverse events and found a significant difference between the groups—and therefore a significant link between the LSM variation and the appearance or not of a cardiac event ($p=0.002$). They also showed the prognostic value of an LSM variation higher than or equal to −44% for the prediction of risk by establishing a significant difference between survival probabilities in patients with an LSM variation higher than or equal to −44% and in patients with an LSM variation lower than −44% ($p=0.001$).

In Kobalava et al. (2022), the authors therefore determined that the decrease in LSM between the start and end of hospitalization was an indicator of the level of congestion of the heart—or rather the level of decongestion of the heart, linked to the treatment received. In this article, the aim is therefore to quantify, using LSM values before and after hospitalization and treatment, the evolution of the cardiac function.

Various aspects of the present invention differ significantly from what has been reported in the literature. An aspect of the present invention allows a rapid non-invasive assessment of a subject's cardiac function at a given moment using LSM. Therefore, it is not a question of evaluating how chronic treatment administration modifies the degree of congestion in a subject. It will be appreciated that an aspect of the invention can be used to assess the cardiac function in individuals with cardiac disease but no evident symptoms of heart failure, as well as in individuals with suspected cardiac illness or predisposed to heart disease that may result in heart failure.

In an aspect of the present invention, the assessment of the cardiac function is performed by using the variation of the LSM of a subject before and after a predetermined cardiac stimulation, in a very much shorter time compared to the length of the state of the art (typically a few seconds or minutes to a few hours, compared to several days or weeks). In other words, one of the aspects of the present invention is directed to assessing the cardiac function in a single procedure using a non-invasive test performed at two closely spaced intervals.

The inventors have indeed determined and developed relevant indexes for evaluating cardiac function, the relevant indexes being constructed from two LSM values before and after carrying out a predetermined cardiac stimulation as defined above. This was far from obvious from the teachings of the aforementioned articles, none of which suggest that two values of the LSM determined over such a short time interval (and which would not necessary be linked to treatment against heart failure) could be used to assess the cardiac function of a subject.

An aspect of the invention therefore relates to a method for determining an index or cardiac function index for assessing a cardiac function of a subject, the method comprising:
performing, by elastography, a first liver stiffness measurement to obtain a first value of a liver stiffness parameter of the subject, the first value being associated with a first time;
performing, by elastography, a second liver stiffness measurement to obtain a second value of the liver stiffness parameter of the subject, the second value being associated with a second time strictly greater than the first time;
determining or computing, by a processing circuit, the index of the cardiac function based on the first value and the second value, and displaying, via a graphical user interface of a display, a visual indicator associated with the determined index of the cardiac function to estimate a cardiac function of the heart of the subject.
wherein the first value corresponds to a value of the liver stiffness parameter obtained before or immediately after carrying out a predetermined cardiac stimulation that modifies a cardiovascular system of the subject and the second value corresponds to a value of the liver stiffness parameter that is obtained after performing the first liver stiffness measurement and the predetermined cardiac stimulation, and
wherein a value of a difference between the second time and the first time is at most 6 hours.

In an embodiment, the index of the cardiac function is configured to be indicative of a degree of congestion of the heart of the subject.

In an embodiment, the value of the difference is at most 5 hours. In another embodiment, the value of the difference is at most 4 hours. In yet another embodiment, the value of the difference is at most 3 hours. In an embodiment, the value of the difference is at most 2 hours. In another embodiment, the value of the difference is at most 1 hour. In another embodiment, the value of the difference is at most 30 minutes, such as at most 15 minutes, and in an embodiment at most 10 minutes, for example at most 5 minutes or even at most 2 minutes. In an embodiment, the first and second liver stiffness measurements are carried out with the same elastography device. It will be appreciated that the first and second liver stiffness measurements could be carried out with two separate elastography devices.

The inventors have indeed determined that the modifications of the LSM following the predetermined cardiac stimulation make it possible to evaluate a heart condition of the subject and thereby determine the presence or the risk of any underlying cardiac dysfunction in this subject.

This beneficially makes it possible to evaluate the cardiac function of a subject very quickly (in a few minutes in some embodiments) and without requiring any invasive procedure since LSM is performed non-invasively. In particular, such an index (referred to as Cardio-Hepatic Congestion—CHC—index) makes it possible to determine liver congestion in an individual patient, which indicates impaired heart function.

These are recent, not-yet published work by some of the inventors of the present application which prompted them to seek an index for evaluating cardiac function based on the LSM. Indeed, as detailed for instance in the not-yet published patent application Ser. No. 18/152,516 filed on Jan. 10, 2023 assigned to the applicant, the inventors have found that the stiffness of a region of a subject's liver was not, contrary to what one might think, a constant value, but, instead, it varies over time. In particular, it was found that the variations of a cardiac signal over time can be found in the measurement of the stiffness of the liver. More specifically, it was found by the inventors that temporal variations of the Central Venous Pressure (CVP) are found in the temporal LSM signal. Therefore, since blood pressure can fluctuate rapidly within a matter of seconds in case of a cardiac dysfunction, the inventors of the present invention have devised that such fluctuations should be observed in the LSM signal.

Since the work of application Ser. No. 18/152,516 filed on Jan. 10, 2023, the inventors of the present invention have further established that the LSM was mainly influenced by three components: a component linked to fibrosis, a component linked to inflammation and a component linked to congestion. In the context of the present invention, at least two measurements of the Liver Stiffness are used to establish the subject's cardiac function assessment index, these at least two measurements being carried out during a relatively short time interval (less than 6 hours). During such a time interval, it is very unlikely that the component linked to fibrosis and the component linked to inflammation vary. Thus, it is mainly the component linked to congestion that can vary from one measurement to another after carrying out the predetermined cardiac stimulation, which makes it possible to assess the cardiac function, eliminating any possible bias linked to other variables known to influence LSM.

By "assessing a cardiac function", it is meant assessing the ability of the heart to meet the metabolic demands of the body. It is therefore understood that "assessing a cardiac function" includes assessing a potential cardiac dysfunction. It is noted that the determined index makes it possible to assess cardiac function, and therefore potentially to detect a risk of cardiac dysfunction, but it does not make it possible to determine what type of dysfunction it is. Typically, a subject with an index suggesting a high risk of cardiac dysfunction will require additional testing to confirm and identify the dysfunction. In particular, the determined index provides an indication of the degree of congestion of the heart, which is directly related to heart function.

By "subject", it is meant any human or animal individual.

By "liver stiffness parameter", it is meant any parameter relating to the liver stiffness of the subject. For example, the liver stiffness parameter may be a liver stiffness measurement, but also other parameters relating to physical quantities such as elasticity, Young's modulus, shear modulus, shear wave speed, viscoelasticity, viscosity or any composite biomarker deriving from (or combining) one or more of the previous physical quantities.

The values of the liver stiffness (LS) parameter may be obtained by any elastography technique, for example transient elastography (such as vibration-controlled transient elastography), acoustic radiation force based elastography, or magnetic resonance elastography.

By predetermined cardiac "challenge" or "stimulation", it is meant a predetermined event to which the subject's heart is subjected. Thus, a predetermined cardiac stimulation is a predetermined event that is specifically designed to modify, and is capable of modifying, certain functional characteristics of the heart, which in turn induce a significant and detectable change in a value of the liver stiffness that can be used to determine a reliable index of the cardiac function in a short time (i.e. at most 6 hours and in some embodiments at most a few minutes) to assess a heart condition of the subject. This differs from other cardiac stimulations induced by a movement of the subject that might not be sufficient to determine a reliable index of the cardiac function in a short time. Changes in these functional characteristics may reveal a dysfunctional heart. Phenotypic manifestation of such dysfunction is congestion. In one or more embodiments, the predetermined cardiac stimulation is carried out by the patient following an instruction from a health care professional, such as a physician and/or an operator of the elastography system that is specifically constructed and arranged to determine the index of the cardiac function of the subject.

By "immediately after" the predetermined cardiac stimulation, it is meant that the first time associated with the first value may be greater than the time at which the predetermined cardiac stimulation occurs, but it cannot be too far in time from this one. More specifically, the difference between the first time and the time at which the predetermined cardiac stimulation occurs is typically of the order of a few seconds (for example, less than 30 or 45 seconds), possibly a few minutes, but in all cases less than 5 minutes, and in an embodiment less than 2 minutes.

It will be appreciated that the index may be a quantitative index (for example the index may take real values) or a classification index (for example, a class of risk). The wording "computing the index" or "determining the index" therefore designates the calculation or determination of a number, but also the determination of a class or category and/or the classification of the number within a class or a category.

It is noted that, where possible, the first value corresponds to a value of the Liver Stiffness (LS) parameter before carrying out the predetermined cardiac stimulation. In particular, the first value may correspond to a value of the Liver Stiffness (LS) parameter "immediately" before carrying out the predetermined cardiac stimulation, i.e. a few seconds to a few minutes before the predetermined cardiac stimulation (e.g. less than 5 minutes before the predetermined cardiac stimulation).

However, it is not always optimal to measure the LS parameter before carrying out the predetermined cardiac stimulation, because it is recommended—when possible— to measure the LS parameter when the subject is in a lying supine position. Therefore, if the predetermined cardiac stimulation is, for example, a change of position from a standing position to a lying supine position, the first value can be measured "immediately" after carrying out the predetermined cardiac stimulation (when the subject has just lain down), and the second value some time after the first value (a few minutes after for example, such as for example, less than 10 minutes, and in one or more embodiments less than 5 minutes).

As mentioned above, it is believed that over such short periods of time (0 to 6 hours) between the first stiffness measurement and the second stiffness measurement, only the component of liver stiffness linked to congestion is likely to vary—the components linked to fibrosis and/or inflammation remaining constant. Thus, the analysis of the variation between the first value of the parameter LS and the second value of the parameter LS provides an indication of the degree of congestion of the subject, and therefore of his/her cardiac function.

Thanks to various aspects of the invention, it is thus possible to evaluate the cardiac function of a subject (and therefore to detect a potential dysfunction) in a non-invasive manner, according to a protocol that is simple to implement. Additionally, it is easy to keep the same measurement location for the elastography procedure. It will be appreciated that various aspects of the invention can be used even on subjects or patients with limited mobility and/or frail subjects or patients. Such an index can be easily interpreted and provide information in a very short time on the state of the subject's heart.

In one or more embodiments, the first time may correspond to a time at which the first liver stiffness measurement is carried out and the second time may correspond to a time at which the second liver stiffness measurement is carried out.

In one or more embodiments, the predetermined cardiac stimulation may comprise at least one of:
 a change of position of the subject;
 a training exercise performed by the subject; and
 an injection of a substance modifying an hemodynamic property of the subject.

In one or more embodiments where the predetermined cardiac stimulation is a change of position of the subject, the value of the difference between the second time and the first time may be at most 15 minutes.

For example, the change of position may be at least one of:
 a change from a standing position to a supine position or a change from a supine position to a standing position;
 a change from a Trendelenburg position to a supine position or a change from a supine position to a Trendelenburg position;
 a change from a supine position in which at least one leg of the subject is lowered to a supine position in which the at least one leg of the subject is elevated, or a change from a supine position in which at least one leg of the subject is elevated to a supine position in which the at least one leg of the subject is lowered; and
 a change from a Fowler's position to a supine position or a change from a supine position to a Fowler's position.

By "supine position", it is meant a position in which the subject lies on his back (with the face and torso facing up). In the supine position, the legs of the subject can be lowered or elevated (or one leg can be lowered and the other elevated). Therefore, in one or more embodiments, the change of position may comprise elevating an initially lowered leg or lowering an initially elevated leg.

It is desirable to measure the LS measurement while the subject is in a lying position. Therefore, in one or more embodiments, the first value and the second value may be measured while the subject is in a supine position, a Trendelenburg position, or a position in which at least one leg of the subject is elevated.

When the predetermined cardiac stimulation is a change from a Trendelenburg position to a supine position, or
 a change from a supine position in which at least one leg of the subject is lowered to a supine position in which the at least one leg of the subject is elevated, or a change from a supine position in which at least one leg of the subject is elevated to a supine position in which the at least one leg of the subject is lowered, or
 a change from a Fowler's position to a supine position or a change from a supine position to a Fowler's position, or
 a change from a supine position to a standing position,
 the first value may correspond to a value of the liver stiffness parameter before carrying out the predetermined cardiac stimulation. Indeed, for such position changes, the subject is in a lying position before carrying out the predetermined cardiac stimulation, that is to say in a preferential position for measuring LSM.

When the predetermined cardiac stimulation is a change from a standing position to a supine position, the first value may correspond to a value of the liver stiffness parameter immediately after carrying out the predetermined cardiac stimulation (e.g. less than 30 seconds after carrying out the predetermined cardiac stimulation, and, in an embodiment, less than 15 seconds after carrying out the predetermined cardiac stimulation).

In various embodiments, the predetermined cardiac stimulation may comprise a predetermined training exercise.

The predetermined training exercise may comprise a series of "classic" bodybuilding or gym movements (jumps, squats, lunges, crunches, burpees, etc.), brisk walking, running on a treadmill, etc.

In these embodiments, the first value may correspond to a value of the liver stiffness parameter before carrying out the predetermined cardiac stimulation. The first value may be measured for example on a patient lying, for example, in supine position.

When the predetermined cardiac stimulation comprises a predetermined training exercise, the value of the difference between the second time and the first time may be comprised between 0 and 30 minutes, for example.

In complement, the predetermined cardiac stimulation may further comprise an administration of an inotropic, vasoconstricting or vasodilating substance.

In this case, the value of the difference between the second time and the first time may be comprised between 0 and 4 hours, i.e. at most 4 hours, for example.

In one or more embodiments, the predetermined cardiac stimulation may comprise an injection of a substance that is specifically designed to modify a hemodynamic property of the subject, which in turn induces a significant and detectable change in a value of the liver stiffness that can be used to determine a reliable index of the cardiac function in a short time (i.e. at most 6 hours and in some embodiments at most a few minutes) to assess a heart condition of the subject, for example a degree of congestion of the heart. In this embodiment, the predetermined cardiac stimulation corresponds to a fluid induced predetermined cardiac stimulation or a hemodialysis.

A fluid induced cardiac stimulation corresponds to an injection of a fluid, for example crystalloids, such as a saline solution, or colloids, in the blood system of the subject, for a short time, for example less than 45 minutes.

Depending on the type of substance injected, the difference between the second time and the first time may significantly vary. For example, the predetermined cardiac stimulation can be an injection of dopamine or dobutamine, or both, for which the heart's response can be detected very quickly, for example within 10 seconds or 15 seconds. In such an example, the value of the difference between the second time and the first time may be less than 1 minute.

For other substances, this difference may be greater, for example by a few hours. In an embodiment, the difference is less than 3 hours (even if for specific cases, it can be between 3 hours and 6 hours).

In one or more embodiments, the index may be a function of a difference between the first value and the second value.

In one or more embodiments, the computation of the index may be further based on the first time and the second time.

In one or more embodiments, the method may further comprise:
 obtaining a set of at least one additional value of the liver stiffness parameter of the subject, each additional value being associated with a time comprised between the first time and the second time;
 wherein the computation or determining of the index is further based on the set of at least one additional value.

In these embodiments, the index is determined based on more than two values of the LS parameter. This makes it possible to follow the evolution of the value of the LS parameter with time, for example to check whether the LS parameter has stabilized (or on the contrary to determine that the LS parameter has not stabilized, for example because it continues to increase), and/or to estimate the time after which the LS parameter has stabilized, and/or determine a speed of growth or decrease of variation.

In one or more embodiments, the set of at least one additional value may comprise n−2 values $LSM_2, \ldots, LSM_{n-1}$, n being an integer greater than or equal to 3, and the index may be a function of:

$$\sum_{i=1}^{n} \alpha_i LSM_i$$

where $LSM_1$ designates the first value of the liver stiffness parameter, $LSM_n$ designates the second value of the liver stiffness parameter,
 where $\alpha_i$ are real coefficients such as:

$$\sum_{i=1}^{n} \alpha_i = 0.$$

In one or more embodiments, the method may further comprise: receiving an information relating to a selection of the predetermined cardiac stimulation among a plurality of predetermined cardiac stimulations.

In these embodiments, the method may further comprise: upon the reception of the information relating to the selection of the predetermined cardiac stimulation, determining the second time associated with the second liver stiffness measurement.

Another aspect of the invention relates to an elastography system for determining an index for assessing a cardiac function of a subject, the elastography system comprising:
 an elastography device configured to perform liver stiffness measurements;
 a processing circuit to receive liver stiffness measurement data from the elastography device, the processing circuit including a processor and a non-transitory memory coded with machine readable instructions that, when executed by the processor, determines the index of the cardiac function based on a first value of a first liver stiffness parameter measured by the elastography device at a first time and a second value of the liver stiffness parameter measured by the elastography device at a second time strictly greater than the first time, and a display including a graphical user interface that is configured to display a visual indicator associated with the determined index of the cardiac function that provides an estimate of a cardiac function of the heart (or heart condition) of the subject, wherein the first value corresponds to a value of the liver stiffness parameter before or immediately after carrying out a predetermined cardiac stimulation that modifies a cardiovascular system of the subject and the second value corresponds to a value of the liver stiffness parameter that is obtained after carrying out the first liver stiffness measurement and the predetermined cardiac stimulation;

wherein a value of a difference between the second time and the first time is at most 6 hours.

In one or more embodiments, the computing module or processing circuit may be further configured to determine a heart condition based on the index computed and on at least one threshold;

wherein the device further comprises a display screen configured to display via a graphical user interface a visual indicator relative to the determined heart condition.

This heart condition represents a level of risk of heart dysfunction for the subject. For example, in one or more embodiments, the determined index can be compared to a predetermined plurality of ranges of values to classify and characterize the determined index. For example, the heart condition may be a classification variable that can take as values: "normal", "below normal" or "abnormal". As a non-limiting example, in one or more embodiments, when the value of the determined index is in a first predetermined range of values, the heart condition of the subject is considered to be "normal"; when the value of the determined index is in a second predetermined range of values, the heart condition of the subject is considered to be "below normal"; and when the value of the determined index is in a third predetermined range of values, the heart condition of the subject is considered to be "abnormal." It will be appreciated that additional or less predetermined plurality of ranges of values could be used in other embodiments to classify and characterize the determined index. Moreover, the classification and characterization of the index may be conveyed to the user in various manners by the elastography system, such as by one or more of displaying a text or letter (e.g., "abnormal" as noted above), displaying a color, displaying a number, and emitting a sound.

In one or more embodiments, the predetermined plurality of ranges of values of the index may be constructed based on existing liver stiffness measurement values for which it is expected that the values, differences of values or combinations of values characterize the heart condition.

In one or more embodiments, the predetermined plurality of ranges of values of the index may also be constructed based on available physiological data obtained from various subjects or patients and that are indicative of various heart conditions. Examples of physiological data can include one or more data obtained from a pulse measurement, a blood pressure measurement, an echocardiogram, an electrocardiogram, a right heart catheterization measurement, a stress test, magnetic resonance imaging, and cardiac computed tomography measurements.

In addition, the display screen may be further configured to display, via a graphical user interface, the computed index, alone or together with the determined heart condition.

For example, the display screen may be configured to display a visual indicator associated with the determined index to estimate a cardiac function of the heart of the subject.

In one or more embodiments, the computing module or processing circuit may be further configured to obtain at least one information relative to:

a fibrosis parameter of the subject;
a biological parameter of the subject; and/or
an anthropometric parameter of the subject;

and the computing module or processing circuit may be configured to determine the at least one threshold and/or the heart condition based on the obtained information.

By "anthropometric parameter", it is meant any parameter relative to a dimensional characteristic of a subject.

This information makes it possible to interpret the values of the LS parameter more precisely, taking into account characteristics specific to the subject and likely to influence the value of the LS parameter.

In one or more embodiments, the above device may be an elastography device.

In these embodiments, the determination of the index is therefore performed by the elastography device.

In one or more embodiments, the display screen is further configured to display a plurality of selectable predetermined cardiac stimulations.

Alternatively, the determination of the index may be performed by a separate device, connected to or in communication with an elastography device (in order to receive the values of the LS parameter).

Another aspect relates to a computer program product comprising a non-transitory computer readable medium, having thereon a computer program comprising program instructions. The computer program is loadable into a data-processing unit and adapted to cause the data-processing unit to carry out the method described above when the computer program is run by the data-processing unit.

Other features and benefits of the method and apparatus disclosed herein will become apparent from the following description of non-limiting embodiments, with reference to the appended drawings.

BRIEF DESCRIPTION OF THE DRAWINGS

Aspects of the present invention is illustrated by way of example, and not by way of limitation, in the figures of the accompanying drawings, in which like reference numerals refer to similar elements and in which.

DETAILED DESCRIPTION

Figure 1:
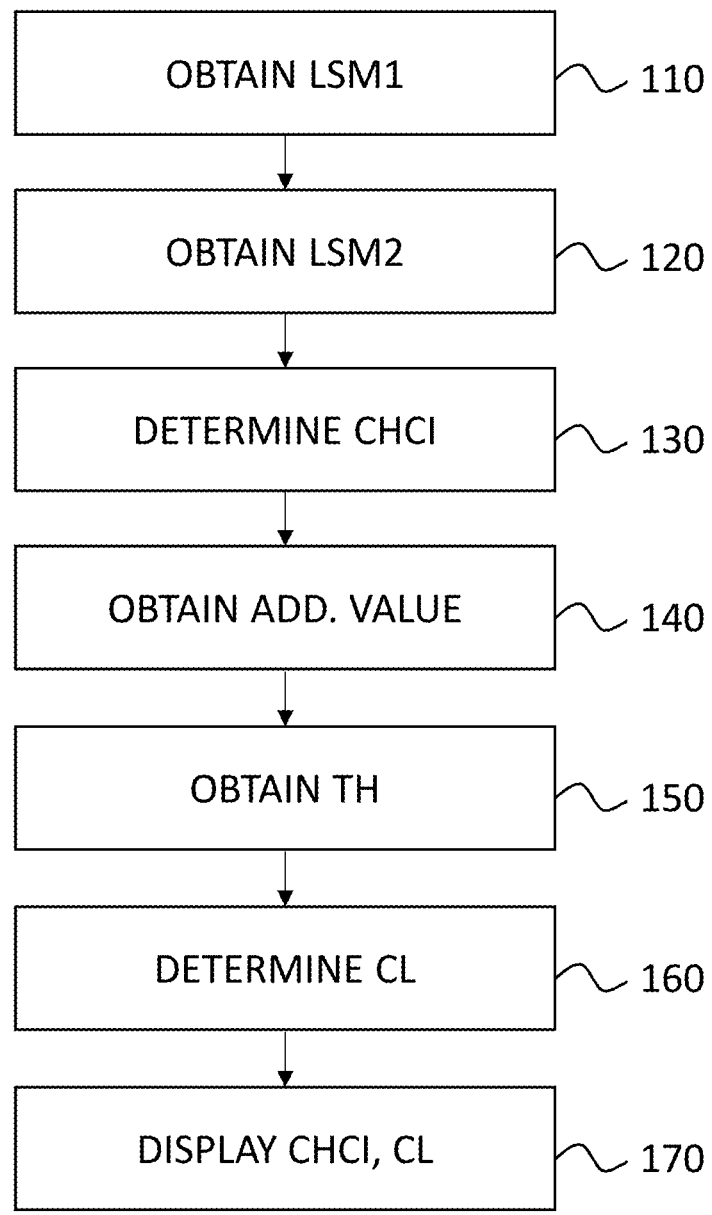
FIG. 1 is a flow chart describing an embodiment of the invention.

FIG. 1 is a flow chart describing an embodiment of the invention. As detailed hereinafter, the steps of FIG. 1 may be carried out by a computing module or processing circuit integrated to an elastography device or connected to an elastography device or in communication with the elastography device. In an embodiment, the computing module or processing circuit includes electronic circuitry to perform the different functions of the computing module or processing circuit.

In a first step 110, a first liver stiffness measurement is performed to obtain a first value of a Liver Stiffness (LS) parameter of a subject. This first value $LSM_1$ is associated with a first time $t_1$.

In step 120, a second liver stiffness measurement is performed to obtain a second value of the LS parameter of the subject. This second value $LSM_2$ is associated with a second time $t_2$ strictly greater than $t_1$: $t_2 > t_1$.

Figure 6:
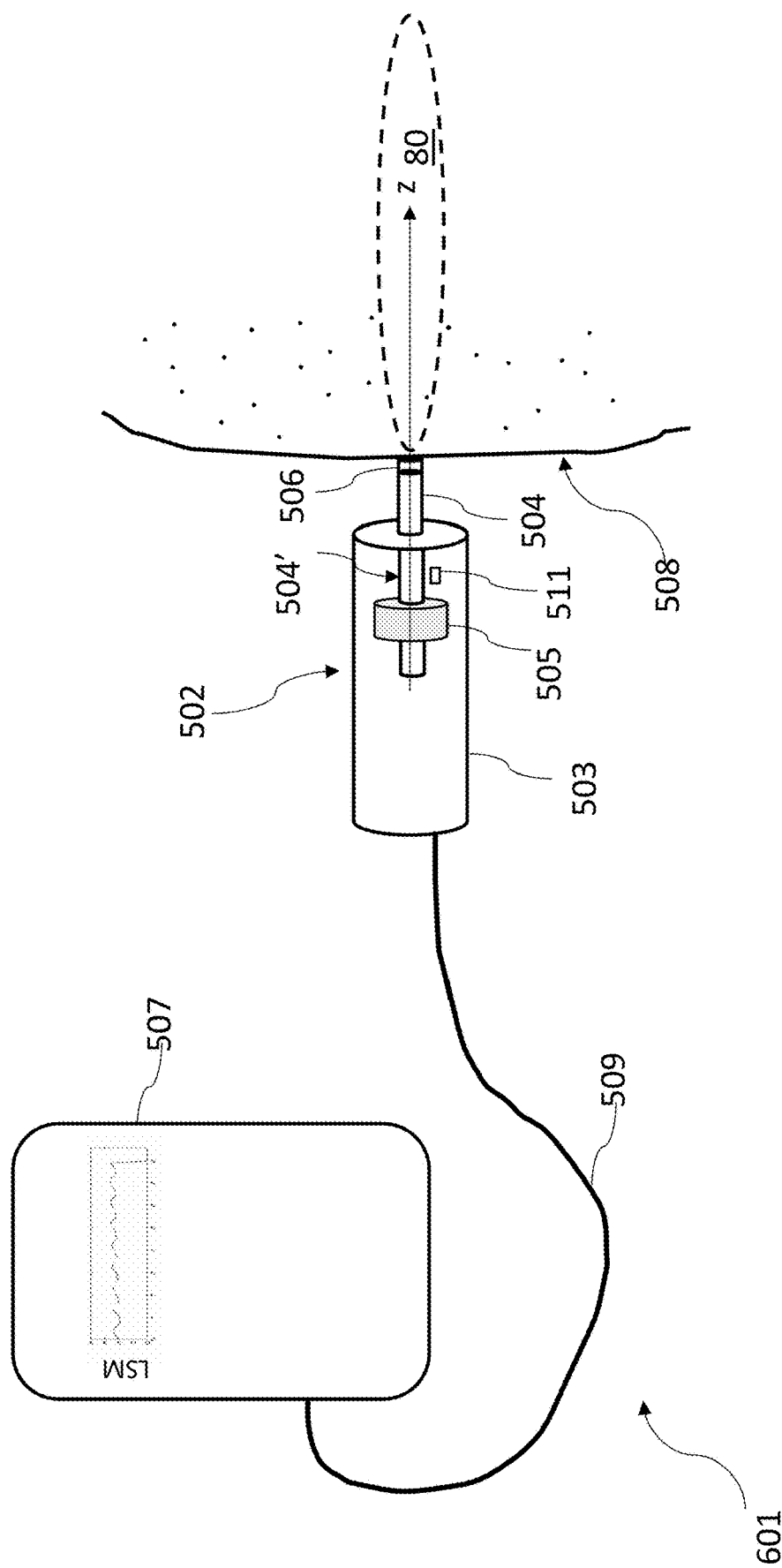

The first and second liver stiffness measurements are performed by elastography using an elastography device. For example, the first and second liver stiffness measurements can be carried out by transient elastography (such as vibration-controlled transient elastography), acoustic radiation force based elastography, or magnetic resonance elastography. An example of a vibration-controlled transient elastography that is adapted to perform the first and second liver stiffness measurements is shown in FIG. 6.

In one or more embodiments, the elastography device comprises a measurement probe and a processing circuit and one or more non-transitory memories coded with instructions to perform various functions, steps, procedures or acts of the methods and devices or elements of the devices disclosed herein.

In one or more embodiments, the elastography device further comprises a display and a graphical user interface. The display and graphical user interface may be controlled by the processing circuit to cause the graphical user interface to display visual information to prompt the operator of the elastography device to carry out the first and the second liver stiffness measurements at predetermined times. The graphical user interface of the elastography device may also be configured to prompt the operator to initiate one or more predetermined cardiac stimulations to the subject/patient under examination. For example, in one or more embodiments, the graphical user interface of the elastography device may be configured to display a drop-down menu or menu including a plurality of selectable predetermined cardiac stimulations to be performed by the subject/patient under examination. In one or more embodiments of the invention, each of the selectable predetermined cardiac stimulations to be performed by the subject/patient is associated with a specific first time t1 and/or second time t2 at which the first and/or second liver stiffness measurements should be carried out. The specific first time t1 and/or second time t2 associated with the selectable predetermined cardiac stimulations may be automatically adjusted based on additional parameters inputted into the elastography device by the operator of the elastography device. As a non-limiting example, the additional parameters may include the age, height, weight, body mass index (BMI), body surface area (BSA), fat mass index, waist circumference, presence of sarcopenia, Frailty indexes or scores, right or left ventricle ejection fraction, right or left atrium diameter or volume, inferior vena cava diameter, circulating BNP and/or pro-BNP of the patient/subject where BNP refers to B-type Natriuretic Peptide.

In one or more embodiments of the invention, the liver stiffness measurements may be triggered automatically or manually. In one or more embodiments of the invention, the selection of a predetermined cardiac stimulation via the graphical user interface may trigger a routine executed by the processing circuit that prompts the operator of the elastography device to a) perform the first liver stiffness measurement at a first time t1, b) initiate the predetermined cardiac stimulation and c) perform the second liver stiffness measurement at a first time t2. For example, in one or more embodiments, the processing circuit of the elastography device may cause the display and graphical user interface to display visual information to instruct the operator to a) perform the first liver stiffness measurement at a first time t1, b) initiate the predetermined cardiac stimulation and c) perform the second liver stiffness measurement at a first time t2. Alternatively or additionally, in one or more embodiments, the processing circuit of the elastography device may control and cause a speaker of the elastography device or a speaker of a remote device in communication with the elastography device to instruct the operator of the elastography device to a) perform the first liver stiffness measurement at a first time t1, b) initiate the predetermined cardiac stimulation and c) perform the second liver stiffness measurement at a first time t2.

As explained above, it will be appreciated that the predetermined cardiac stimulation b) can be initiated prior to performing the first liver stiffness measurement at a first time t1 at a). In one or more embodiments of the invention, the graphical user interface is controlled by the processing circuit such that it is configured to display a visual index of the cardiac function based on the first and second measured liver stiffness values.

It is noted that in the above example, the display and the graphical user interface (GUI) are integrated in the elastography device. This is not limiting. In an alternative embodiment, an external device (i.e. external to the elastography device) may comprise a display and a GUI to display visual information to prompt the operator to carry out the first and the second liver stiffness measurements at predetermined times on the elastography device, and to prompt the operator to initiate one or more predetermined cardiac stimulations to the subject/patient under examination. The external device may also comprise a user interface for receiving the values of the measurements thus carried out (for example, the operator can enter these values using a keyboard or a touch screen of the external device).

Referring back to FIG. 1, the first value obtained at step 110 corresponds to a measurement value of the LS parameter obtained before or immediately after the individual is subjected to a predetermined cardiac stimulation that modifies his/her cardiovascular system. By immediately after, it is meant that the first value is associated with a time between T and T+δT, where T is the time at which the predetermined cardiac stimulation occurs or ends. δT is typically of the order of a few seconds, possibly a few minutes, but in all cases less than 5 minutes, and in an embodiment less than 2 minutes. Therefore, the first time $t_1$ associated with the first value $LSM_1$ is such as $t_1 < T$ or $T \le t_1 \le T + \delta T$.

The predetermined cardiac stimulation corresponds to a predetermined event that has an impact on the subject's cardiovascular system such as, but not limited to, a change in heart rate, change in the blood volume in the heart chambers, change in the inotropic activity, change in the blood fluidity, etc. Typically, the predetermined cardiac stimulation can be at least one of:
- the subject changing position (raising at least one leg, moving from a raising position to a lying position, etc.);
- the subject performing physical activity (e.g. performing low to high intensity movements during several minutes), and
- injecting the subject with a substance modifying a hemodynamic property of the subject (vasodilator, vasoconstrictor, saline solution, inotropic solution, etc.).

The above examples may be combined. For example, the predetermined cardiac stimulation may comprise a physical activity, with injection of a substance modifying a hemodynamic property of the subject.

A change of position modifies the blood volume of the heart chambers, which can have a direct impact on possible congestion in subjects with cardiac dysfunction. For example, the change of position may be at least one of:
- a change from a standing position to a supine position or a change from a supine position to a standing position;
- a change from a Trendelenburg position to a supine position or a change from a supine position to a Trendelenburg position;
- a change from a supine position in which at least one leg of the subject is lowered to a supine position in which the at least one leg of the subject is elevated, or a change from a supine position in which at least one leg of the subject is elevated to a supine position in which the at least one leg of the subject is lowered, and
- a change from a Fowler's position to a supine position or a change from a supine position to a Fowler's position.

This is not limiting. It will be appreciated that other changes of position are possible. In the examples above, one of the start or finish positions is a lying supine position, because this is the recommended position for measuring a subject's LSM, but other positions are possible.

The predetermined cardiac stimulation may also comprise a physical activity performed by the subject. In this case, the patient is asked to perform one or more series of movements, which can vary from low intensity to high intensity, for several seconds or several minutes. For example, the predetermined cardiac stimulation may be a standardized cardiac stress test, but it is possible to subject the patient to less intense physical activity.

As mentioned above, the physical activity may be combined with the injection of a substance, to increase the stimulation of heart inotropism. The substance may be a dobutamine or other inotropic solution, a saline solution, a vasoconstricting solution or a vasodilating solution. The vasoconstrictor or vasodilator may be for example an arterial vasoconstrictor or vasodilator, a venous vasoconstrictor or vasodilator, or a pulmonary artery vasodilator.

The physical activity may be replaced by an intravenous pharmacological stimulation of heart inotropism. Therefore, the predetermined cardiac stimulation may only include injecting a substance into the patient's body. The substance may be a saline solution, an inotropic solution, a vasoconstricting solution or a vasodilating solution. The predetermined cardiac stimulation may also be a fluid induced stimulation (injection of a fluid, for example crystalloids, such as a saline solution, or colloids, for a short time, for example less than 45 minutes) or a hemodialysis.

When the predetermined cardiac stimulation comprises an injection of a substance into the subject, it is noted that the aim is to rapidly modify cardiac properties, not to evaluate over the long term (for example several days) the effects of a treatment on a cardiac disease.

The second value corresponds to a measurement value of the LS parameter after carrying out the predetermined cardiac stimulation and, in particular, after performing the first liver stiffness measurement. The second value is associated with a second time $t_2$ strictly greater than the first time $t_1$: $t_2 > t_1$.

Depending on the embodiments, this second value corresponds to a measurement of the LSM a few seconds to a few minutes, or even a few hours after performing the predetermined cardiac stimulation.

When possible, the first value corresponds to a value of the LS parameter before carrying out the predetermined cardiac stimulation. But this is not always optimal, for example when the predetermined cardiac stimulation is "moving the subject from a standing position to a lying position", because it is not recommended to measure the LS on a standing subject. Thus, in this last example, the subject is kept in a standing position for a certain time, then he may be asked to lie down. The first value of LS is measured just after he has lain down, and the second value from LS a few minutes later.

In any case, in the context of the invention, the difference between the second time and the first time is comprised up to 6 hours, such as:

$0 < t_2 - t_1 < 6$ hours.

The LS parameter may be any parameter related to the LS of the subject.

In one or more embodiments, the LS parameter corresponds to a single value of the LS measurement (LSM). For example, each value LSM (with $i \in \{1,2\}$) may correspond to the LSM of the subject carried out at the respective time $t_i$.

In alternative embodiments, the LS parameter $LSM_i$ may be computed from a series of LS measurements $\{LSM_i^j\}_{j=1,\ldots,J}$, J being an integer strictly greater than 1. For example, this series of measurements may be collected at a predefined frequency (e.g. from 4 measurements per second to 1 measurement every k second, with k an integer between 1 and 5, depending on the elastography technique used) when the operator triggers measurements. The LS parameter may be derived to any statistical parameter(s) determined from this series of measurements. Classically, the LS parameter may correspond to the mean or the median of the series of measurements, but other statistical parameters may be used. The parameter may also be a combination of several statistical parameters, for example a combination of at least one position parameter (mean, median, quantile, minimum, maximum, . . . ), eventually combined with at least one dispersion parameter (standard variation, coefficient of variation, . . . ). The time $t_i$ associated with the value $LSM_i$ may be the time at which the series of measurements is triggered (which may correspond to the time at which the first measurement is obtained, eventually delayed by a predefined offset), but other embodiments are possible. For example, the time may be defined as the time at which the last measurement of the series of measurements is obtained, of the average time between the first measurement of the series of measurements and the last measurement of the series of measurements.

In yet other embodiments, the elastography device is configured to obtain a signal LSM(t) representative of variations of LSM with time, as described for example in patent application Ser. No. 18/152,516 filed on Jan. 10, 2023. In these embodiments, the LS parameter may be a function of a maximum, a minimum, a mean, a standard deviation and/or a percentile of the obtained signal LSM(t). For example, each value $LSM_i$ ($i \in \{1; 2\}$) of the LS parameter may be determined from the signal LSM(t) measured during a time interval $\Delta T_i=[t_{start}^i; t_{end}^i]$, e.g. the mean or the amplitude of the LSM signal during the time Interval $\Delta T_i$. For example, the time $t_i$ associated with the value $LSM_i$ may correspond to $t_{start}^i$ or $t_{end}^i$ (eventually delayed by a predefined offset), to the average time $(t_{end}^i-t_{start}^i)/2$ of $\Delta T_i$, or to any other time related to time interval $\Delta T_i$.

Some examples of predetermined cardiac stimulations are now provided to illustrate one or more embodiments of the invention. These examples are not limiting.

In a first example, the predetermined cardiac stimulation corresponds to a change of position from a standing position to a lying supine position. As it is not recommended to perform LS measurements in standing position, the first value $LSM_1$ of the LS parameter can be associated with a time $t_1$ immediately after the change of position, when the patient is lying. For example, the first value $LSM_1$ may be measured within 5 to 90 seconds after position change. The second value $LSM_2$ of the LS parameter can be associated with a time $t_2$ within 1 to 5 minutes following $t_1$.

In this first example, it is expected that the difference between the second value and the first value is low in healthy subjects, and high in patients with cardiac dysfunction or heart failure.

In a second example, the predetermined cardiac stimulation corresponds to a change of position from a lying supine position to a reclined Trendelenburg position. The first value $LSM_1$ can be measured in the lying supine position (i.e. before the position change, for example 1 to 15 minutes before the position change). The second value can be measured immediately after the position change, i.e. just after the subject is in the Trendelenburg position (for example, within 5 minutes following the position change).

In these two first examples, the predetermined cardiac stimulation is a change of position, which typically lasts a few seconds.

In a third example, the predetermined cardiac stimulation corresponds to a physical exercise to which the subject is subjected. For example, the physical exercise may comprise a series of movements, like squats, lunges, crunches, burpees, etc., or any combination of these movements. In this example, the predetermined cardiac stimulation (i.e. the physical exercise) can typically last from a few minutes to a few tens of minutes, for example between 5 minutes and 30 minutes. The first value $LSM_1$ can be measured in the lying supine position before the physical exercise. The second value can be measured in the lying supine position after the physical exercise (for example, within 15 minutes following the end of the physical exercise).

In a fourth example, the predetermined cardiac stimulation corresponds to a dialysis procedure. In this example, the predetermined cardiac stimulation typically lasts few hours, for example 3 to 5 hours. The first value $LSM_1$ can be measured in the lying supine position before the dialysis starts. The second value can be measured in the lying supine position after the dialysis ends (for example, within 15 minutes following the end of the dialysis).

In a fifth example, the predetermined cardiac stimulation corresponds to a fluid induced stimulation, i.e. an injection of a substance into the blood of the patient. The substance may be for example a saline solution, a vasodilating or vasoconstricting substance or an inotropic substance. In this example, the predetermined cardiac stimulation may last few minutes to few hours, for example 1 minute to 3 hours. The first value $LSM_1$ can be measured in the lying supine position before the injection of the substance starts. The second value can be measured in the lying supine position after the injection of the substance ends (for example, within 15 minutes following the end of the injection).

Referring again to FIG. 1, in step 130, an index, referred to as Cardio-Hepatic Congestion index CHCI (or CHC index), for assessing the cardiac function of the subject is computed or determined as a function of the first value of the LSM parameter and the second value of the LSM parameter: $CHCI=f(LSM_1, LSM_2)$. In one or more embodiments, the index is determined using a processing circuit of the elastography device. Alternatively, the index is determined using a processing circuit of a remote electronic terminal or a remote server that is communication with the elastography device. In this latter implementation, the remote electronic terminal or remote server and the elastography device can communicate via a wired link or a wireless link, such by Wi-Fi, BLUETOOTH® (a short-range wireless technology standard), ZIGBEE Ethernet, . . . ). Depending on embodiments, the CHC index may take real values or integer values. For example, the CHC index may take any real values, or real values strictly greater than 0, or real values between −1 and 1 or between 0 and 1. In embodiments, the CHC index may be a classification (or "qualitative") variable (for example a class of risk or severity of cardiac dysfunction).

In some embodiments, the higher the value of the index, the more the subject presents a risk of cardiac dysfunction. Conversely, the closer the index is to 0, the less the subject presents a risk of cardiac dysfunction, and therefore "correct" cardiac function.

It will be appreciated that the CHC index may be defined so that a value close to 0 corresponds to a high risk of cardiac dysfunction, and a high value of the index corresponds to a low risk of cardiac dysfunction.

The CHC index reflects the variation of the LS parameter caused by the predetermined cardiac stimulation, which can potentially induce either heart congestion or decongestion.

In embodiments, the CHC index is function of a difference $\Delta_{LSM}$ between the second value of the LS parameter and the first value of the LS parameter:

$$CHCI=f(\Delta_{LSM})$$

with $\Delta_{LSM}=LSM_2-LSM_1$.

For example, the CHC index may be defined as:

$$CHCI=\Delta_{LSM}=LSM_2-LSM_1.$$

In this example, the CHC index represents the variation of the LS parameter induced by the predetermined cardiac stimulation.

This index can also be divided by a reference value homogeneous to a modulus, to be made unitless, for example:

$$CHCI = \frac{LSM_2 - LSM_1}{10 \text{ kPa}}.$$

In alternative or complementary embodiments with the previous ones, the CHC index can further be calculated from the times $t_1$, $t_2$ associated with the values $LSM_1$, $LSM_2$ of the LS parameter: $CHCI=f(LSM_1, LSM_2, t_1, t_2)$.

For example, the CHC index may correspond to (or be a function of) the rate of change of the LS parameter, defined as follows:

$$CHCI = \frac{LSM_2 - LSM_1}{t_2 - t_1}.$$

Other forms of functions may be used to define the CHC index. For example, the CHC index may be of the form of a logistic equation, such as:

$$CHCI = \frac{e^{\beta \ln\left(\frac{LSM_2}{LSM_1}\right)}}{1 + e^{\beta \ln\left(\frac{LSM_2}{LSM_1}\right)}}$$

where $\beta$ is a real coefficient.

The time T at which the predetermined cardiac stimulation occurs may also be used to compute the CHC index: CHCI=$f$(LSM$_1$, LSM$_2$, t$_1$, t$_2$, T).

In all examples provided above, it is possible to take the absolute value of the formulas, to obtain a positive index. Also, all the formulas above may be multiplied by a constant coefficient to reduce the possible values to a certain interval of values. This coefficient may also be proportional or inversely proportional to a baseline LS value (e.g. one of the values of the LS parameter) to compensate for the influence of baseline liver fibrosis on the change in LSM before and after performing the predetermined cardiac stimulation.

Referring again to FIG. 1, in an optional step 140, at least one additional value relating to the subject may be obtained. It is noted that step 140 may be performed before steps 110, 120 and/or 130, or in parallel with these steps.

One additional value may be for example a fibrosis parameter of the subject, e.g. a baseline value of fibrosis of the subject. In particular, this additional value may be a baseline value of the LS parameter—for example, the usual (or "normal") value of the LSM of the subject, which can be high when the subject has a significant level of fibrosis, even in absence of congestion. This baseline value of the LS parameter may be a value of the LS parameter determined after the subject has been lying down for a sufficiently long time (for example a few minutes to a few tens of minutes, for example 15 minutes), so that the LSM value is stabilized. Such a baseline value provides a reference for determining how the heart adapts to the predetermined cardiac stimulation.

Alternatively, or additionally, one additional value may be a biological or an anthropometric parameter of the subject. For example, the additional value comprises at least one blood marker (biological parameter(s)). The anthropometric parameter may be for example the Body Mass Index (BMI), body surface area (BSA), the height, the weight, the age, waist circumference, Fat Mass Index, presence of sarcopenia, right or left ventricle ejection fraction, inferior vena cava diameter, circulating BNP or pro-BNP, etc.

As mentioned above in the case of a baseline LS measurement, such value(s) may be used for determining the CHC index (in this case, step 140 is performed between step 130). Such value(s) may also be used to interpret the value of the CHC index, as detailed hereinafter. Indeed, the level of fibrosis of the subject, as well as certain biological or anthropometric parameters, may influence the average value of the LS parameter of the subject, or how the predetermined cardiac stimulation can impact the value of the LS parameter. Therefore, to avoid interpretation bias linked to confounding factor(s), these parameters may be taken into account to correct or to analyze the value of the CHC index.

When the at least one additional value is used to interpret the CHC index (but not to compute the CHC index), step 140 may be carried out after (or before) step 130.

At an optional step 150, at least one threshold may be obtained. This at least one threshold may be received (e.g. in case of predefined threshold(s)) or determined by the computing module or processing circuit. The at least one threshold obtained at step 150 makes it possible to define heart dysfunction risk classes, and therefore to determine (at step 160) the risk class of the subject based on the value of their CHC index and at least one threshold.

In one or more embodiments, the at least one threshold may be equal to at least one predefined value. For example, when the CHC index corresponds to the absolute value of the difference between the second value and the first value of the LS parameter (i.e. CHCI=|LSM$_2$−LSM$_1$|), two predefined thresholds may be received: Th$_1$ and Th$_2$. If CHCI≤Th$_1$, the subject is considered at "low risk", if Th$_1$<CHCI≤Th$_2$, the subject is considered at medium risk, and if CHCI>Th$_2$, the subject is considered at high risk. For example, Th$_1$=2 kPa and Th$_2$=20 kPa. It will be appreciated that other values may be used, and a number of classes other than 3 can be defined.

In embodiments where the threshold is predefined and received by the computing module, step 150 may be performed before 110, 120, 130 and/or 140, or performed in parallel of one or more of these steps.

In the above example, the threshold(s) is (are) the same for all subjects. Alternatively, it is possible that the predefined thresholds depend on other characteristics, for example an average degree or an average value of fibrosis of the subject, or the BMI (Body Mass Index)/weight/height/body fat index/sarcopenia/etc. of the subject. In such embodiment, the thresholds may vary from one subject to another, depending on their characteristics. These characteristics may correspond to a fibrosis parameter, a biological parameter and/or an anthropometric parameter of the subject. For example, these characteristics may correspond to all or part of the parameters received at step 140.

In embodiments, at step 150 the computing module may therefore determine, based on the additional values received at step 140, the threshold(s). In these embodiments, step 150 is necessarily carried out after step 140.

In other embodiments, the threshold(s) is (are) not predefined value(s), and the computing module is configured to determine the threshold(s) based on reference value(s) and the additional values received at step 140. In these embodiments, step 150 is also necessarily carried out after step 140.

In some of the above embodiments, the additional values received at step 140 are taken into account to determine the threshold(s) to which the CHC index is compared, to assess (step 160) the risk class of the subject. This makes it possible to avoid a bias due to a parameter (e.g. a fibrosis, biological or anthropometric parameter of the subject) which has a link with the value of the LS parameter of the subject.

Alternatively, such "correction" can be made at the level of the CHC index itself rather than at the level of the threshold(s). Therefore, in alternative embodiments, a "corrected" value of the CHC index is determined based on the value determined at step 130 and the additional values received at step 140. To determine (step 160) a class risk for the subject, this corrected CHC index may be compared to threshold(s) obtained at step 150, which are the same for all subjects.

As mentioned above, at an optional step 160, a risk class may be determined based on the CHC index determined at step 130, the threshold(s) obtained at step 150, and eventually the additional value(s) obtained at step 140. The risk class represents the risk, for the subject, of having cardiac dysfunction. It is therefore representative of the cardiac function of the subject. For example, a "high risk" class makes it possible to detect potential cardiac dysfunction, while a "low risk" class reflects normal cardiac functioning.

When the CHC index is a categorical variable, step 150 may be omitted, and the CHC index determined at step 130 and the additional value(s) obtained at step 140 may be used to determine a new risk class at step 160.

Finally, at step 170, the CHC index and/or the risk class may be displayed on a display device controlled by the computing module.

Even if the method of FIG. 1 has been presented in the case where the CHC index is calculated from two values of the LS parameter, it is noted that the invention is not limited to this scenario. For example, in place of steps 110 and 120 of FIG. 2, a set of N values $LSM_1, \ldots, LSM_N$ of the LS parameter may be obtained, with N an integer strictly greater than 2. Each value $LSM_i$, $i \in \{1, \ldots, N\}$ may be associated with a respective time $t_i$, with:

$$t_1 < t_2 < \ldots < t_{N-1} < t_N.$$

At least one value $LSM_i$ corresponds to a value of the LS parameter before or immediately after performing the predetermined cardiac stimulation (as defined above), and at least one value $LSM_i$ corresponds to a value of the LS parameter after performing the predetermined cardiac stimulation. The difference between the last time ty and the first time $t_1$ is lower than 6 hours: $0 < t_N - t_1 < 6$ hours.

This corresponds to a generalization of the case in FIG. 1, in which N=2.

The acquisition of additional LS values makes it possible to follow the evolution of the LSM over time, and thus to determine whether the LSM values stabilize "normally" (i.e. as one would expect from a subject who does not have cardiac dysfunction) or not. In particular, from the set of measurements, it is possible to determine, for example, one or more slopes, or a time constant representing a rapidity with which the patient's hepatic rigidity stabilizes. The CHC index may be determined from these slopes or this time constant. The higher the number of values of the LS parameter, the more precisely the evolution of the LSM can be determined.

In one or more embodiments, the CHC index CHCI may be computed as a function of the first value of the LSM parameter and the second value of the LSM parameter: $CHCI = f(LSM_1, LSM_2, \ldots, LSM_N)$.

For example, the CHC index may be of the form:

$$CHCI = \sum_{i=1}^{N} \alpha_i LSM_i$$

with $\alpha_1, \ldots, \alpha_N$ a set of real weights.

To eliminate the contribution of components other than congestion (components linked to fibrosis and inflammation in particular), the weights $\alpha_1, \ldots, \alpha_N$ can be chosen such as:

$$\sum_{i=1}^{N} \alpha_i = 0.$$

As before, the CHC index can further be calculated from the times $t_1, \ldots, t_N$ associated with the values $LSM_1, \ldots, LSM_N$ of the LS parameter:

$$CHCI = f(LSM_1, LSM_2, \ldots, LSM_N, t_1, t_2, \ldots, t_N).$$

In embodiments, when a series $LSM_1, LSM_2, \ldots, LSM_N$ of values of the LS parameter is obtained, it is possible to compute several values of the CHC index and to analyze the variation of the values of the CHC index with time. Indeed, for certain predetermined cardiac stimulations, in particular predetermined cardiac stimulations comprising a physical activity or the injection of a substance in the blood, the difference "before/after" (in absolute value) is expected to increase and then stabilize.

For example, a series of values $CHCI_k = f(LSM_1, LSM_k)$, $k = 2, \ldots, N$, may be determined, with $LSM_1$ a value of the LS parameter before or immediately after performing the predetermined cardiac stimulations, and $LSM_k$ ($k=2, \ldots, N$) a set of values of the LS parameter after performing the predetermined cardiac stimulation (and after the time associated with $LSM_1$).

In this example, the variations of the value of the CHC index $CHCI_k = f(LSM_1, LSM_k)$ with time may be analyzed to monitor the increase, the decrease or the stabilization of the index, which can provide an indication of the state of health of the subject. Indeed, after performing the predetermined cardiac stimulations, the heart may take a few minutes to adapt, and therefore the LSM may take a few minutes to normalize. Therefore, the evolution of the CHC index $CHCI_k = f(LSM_1, LSM_k)$ and/or the evolution of the values of the LS parameter with time may provide information about the way the heart adapts after performing the predetermined cardiac stimulation, and therefore about the severity of the potential heart dysfunction.

In one or more embodiments, the processing circuit may be configured to determine and output a continuous signal representative of variations of the LSM with time, for example with value measurements of the LS parameter with a frequency greater than 4 measurements per second, such as between 10 and 20 measurements per second. This signal may be adjusted with known functions using for example a polynomial adjustment or an exponential adjustment (or "regression"), using least squares adjustment methods for example.

In the case of an exponential adjustment, the LSM may be approximated by a function:

$$LSM(t) = Ke^{-\frac{t}{\tau}}$$

where $\tau$ is a time constant representative of the speed of stabilization of the LSM value.

In another example, the CHC index may be a categorical value representing a class of severity of a potential heart dysfunction determined based on the series of values $\{LSM_1, LSM_2, \ldots, LSM_N\}$, and more specifically based on the evolution of the values of the values of the LS parameter with time. For example, the CHC index may take one of the following classes: "normal" if the values of the LS parameter stay stable or decrease with time, "moderately severe" if the values of the LS parameter increase then decrease with time, "severe" if the values of the LS parameter increase and then stabilize, and "very severe" if the values of the LS parameter keep increasing.

It is noted that the different classes above could also be determined from the variation of a quantitative CHC index with time rather than the variation of the value of the LS parameter with time.

Figure 2:
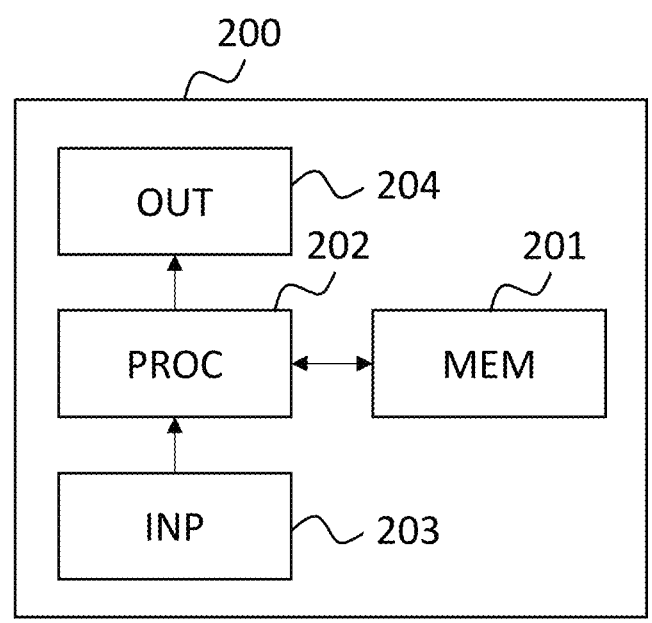
FIG. 2 represents an example of a computing module configured to implement a method for determining an index to assess a subject's cardiac function.

FIG. 2 represents an example of a computing module or processing circuit configured to implement a method for determining an index to assess a subject's cardiac function in one embodiment of the invention.

In this embodiment, the computing module or processing circuit 200 can form at least part of a computer, and includes a non-transitory memory 201 to store program instructions loadable into a circuit 202 (e.g. a microelectronic circuit or circuitry) and adapted to cause circuit 202 to carry out one or several steps of the method(s) or function(s) of the device(s) described herein when the program instructions are executed by the circuit 202.

The memory 201 may also store data and useful information for carrying the steps of the method(s) described herein. The circuit 202 may be for instance:
- a processor or a processing unit adapted to interpret instructions in a computer language, the processor or the processing unit may comprise, may be associated with or be attached to a memory comprising the instructions, or
- the association of a processor/processing unit and a memory, the processor or the processing unit adapted to interpret instructions in a computer language, the memory comprising said instructions, or
- an electronic card wherein the steps of the invention are described within silicon, or
- a programmable electronic chip such as a FPGA chip (for «Field-Programmable Gate Array»).

This computing module or processing circuit 200 further comprises an input interface 203 for receiving values of the LS parameter, and eventually additional value(s) and predefined threshold(s), and an output interface 204 for providing at least the computed value of the CHC index (and eventually the determined heart dysfunction risk class of the subject).

Figure 3:
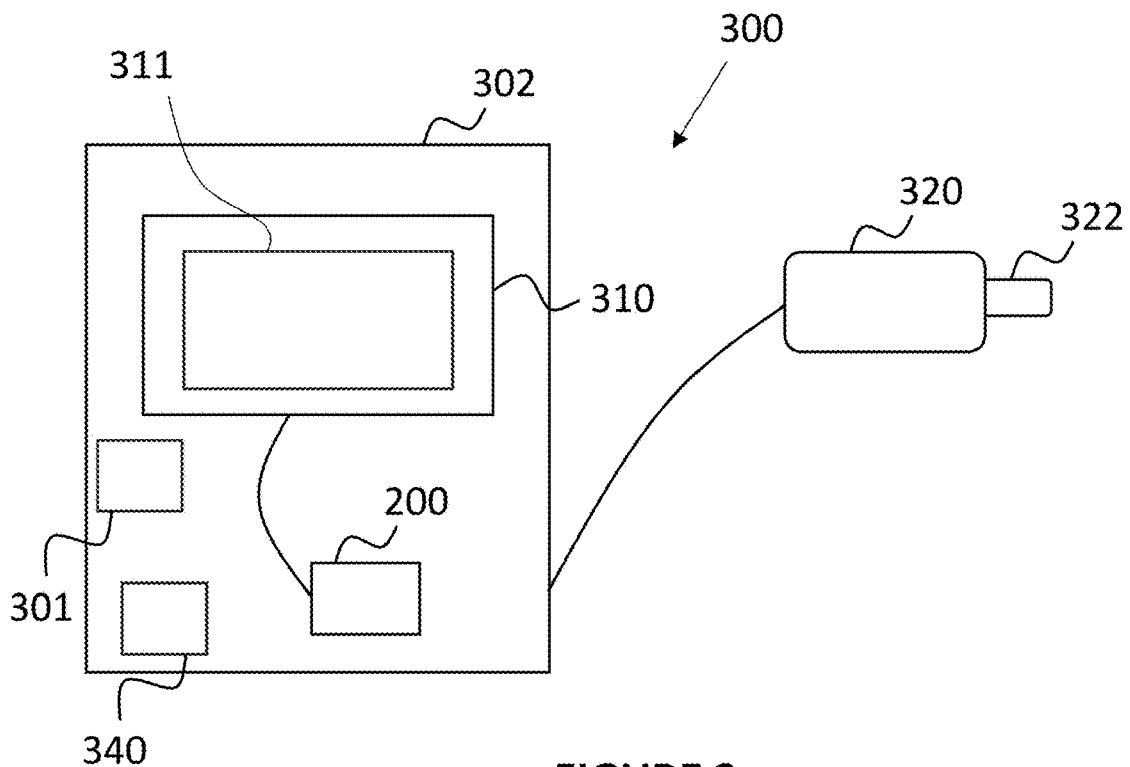
FIG. 3 represents an example of a device for determining an index to assess a subject's cardiac function in an embodiment of the invention.

Optionally, the computer circuit 202 may be connected to or in communication with a screen and may be configured to control the screen and the graphical user interface to cause the graphical user interface to display predetermined information such as, for example, a visual representation of the computed value of the CHC index and/or the determined heart dysfunction risk class of the subject, and/or visual information to instruct the operator of the elastography device to perform one or more steps of the method(s) described herein. The computer circuit 202 may also be configured to control the screen and the graphical user interface to cause the graphical user interface to display additional information, such as, but not limited to, a value of elasticity, a stiffness measurement, a measurement ready signal to indicate that the probe is correctly positioned against the skin of the subject/patient and/or an elastogram and/or patient information such as the age, weight and/or height of the patient. Moreover, in one or more embodiments, the computer circuit 202 may also be configured to control a speaker of the elastography device or a speaker of a remote device in communication with the elastography device to emit audible sounds, such as, but not limited to, audible instructions to instruct the operator of the elastography device to perform one or more steps of the method(s) described herein. FIG. 3 represents an example of a device for determining an index to assess a subject's cardiac function according to an embodiment of the invention.

In this example, the computing module or processing circuit 200 is integrated into an elastography device 300. The elastography device 300 can use any known elastography technique, for example transient elastography, such as vibration-controlled transient elastography (VCTE), shear wave elastography (SWE) or acoustic radiation force impulse (ARFI) elastography, or any other type of elastography, such as magnetic resonance elastography (MRE). A schematic representation of a vibration-controlled transient elastography is shown in FIG. 6.

When the elastography device 300 uses an ultrasound elastography technique, the elastography device 300 may comprise a central unit 302 and an elastography probe 320 provided with an ultrasonic transducer 322 configured to emit and receive ultrasonic waves. The elastography probe 320 is connected to the central unit 302 of the elastography device 300 via a wired link or a wireless link. When the elastography device 300 is configured to perform transient elastography, the probe 320 is further configured to deliver transient, low frequency mechanical pulses.

The elastography device 300 may also comprise a human machine interface (HMI) 301 to receive, for example, at least one additional value (step 140 of FIG. 1) relating to the subject.

The elastography device 300 may comprise a screen 310 for displaying, via a graphical user interface 311, information relating to the patient, for example one or more elastography measurements, but also the CHC index calculated by the calculation module, and/or the heart dysfunction risk class determined. The screen 310 and graphical user interface 311 may be controlled by the computing module or processing circuit 200 or by a separate processing circuit of the elastography device 300 that is in communication with the computing module or processing circuit 200.

In the example of FIG. 3, the computing module or processing circuit 200 which implements the calculation of the CHC index can be a module or circuit dedicated to this, or the same module as the computing module or processing circuit which determines the values of the LSMs.

Figure 4:
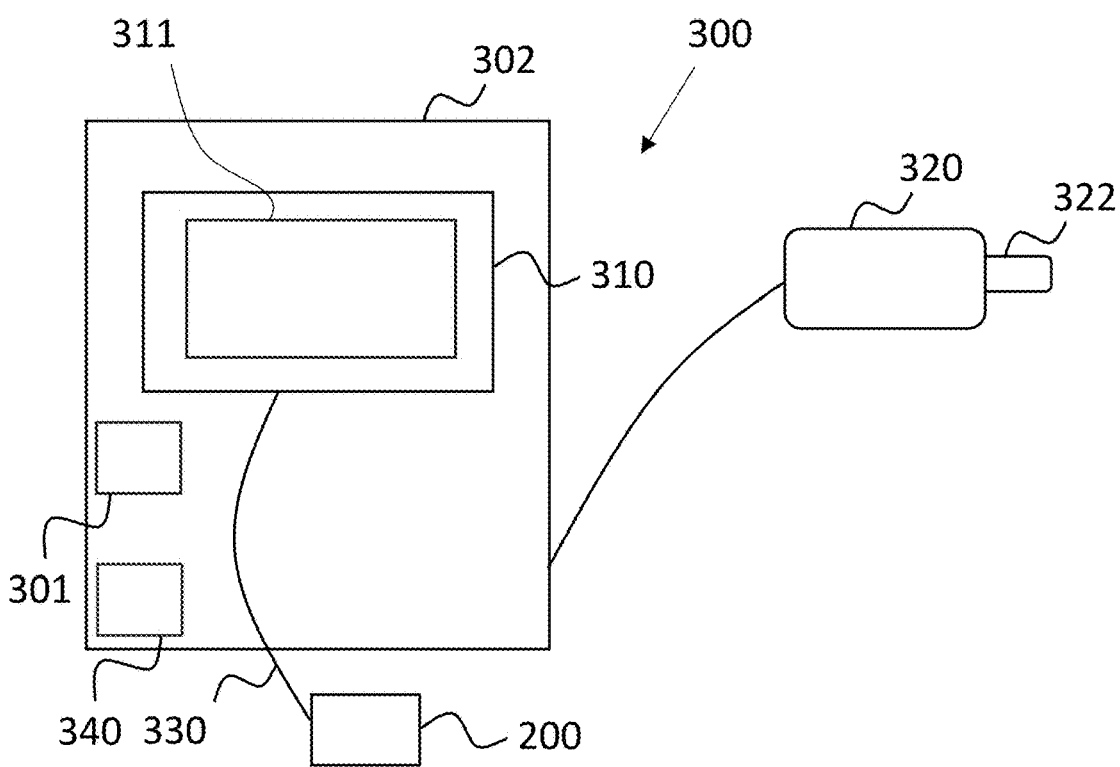
FIG. 4 represents an example of a device for determining an index to assess a subject's cardiac function in another embodiment of the invention.

FIG. 4 represents an example of a device for determining an index to assess a subject's cardiac function in another embodiment of the invention.

Unlike the elastography device of FIG. 3, the computing module or processing circuit 200 of FIG. 4 is external to the elastography device 300. In this embodiment, the computing module or processing circuit 200 is connected via a wired link or a wireless link 330 (such by Wi-Fi, BLUETOOTH® (a short-range wireless technology standard), ZIGBEE, Ethernet, . . . ) to the elastography device 300 to receive values of the LS parameter (determined by the elastography device 300) from the elastography device 300. The computing module or processing circuit 200 is configured to compute the value of the CHC index (and eventually the heart dysfunction risk class) and to transmit this or these value(s) to the elastography device 300, such as to a separate internal module or processing circuit of the elastography device 300. The elastography device 300 can then display this or these value(s) on the screen 310. In this embodiment, the separate internal module or processing circuit of the elastography device 300 can be used to control the display 310 and the graphical user interface 311 of the elastography device 300. Alternatively, as shown in FIG. 5, the computing module or processing circuit 200 may be integrated to a device separated from the elastography device and having its own display or screen and graphical user interface (for example a user equipment, such as a smartphone or a tablet), to display the above information.

Figure 5:
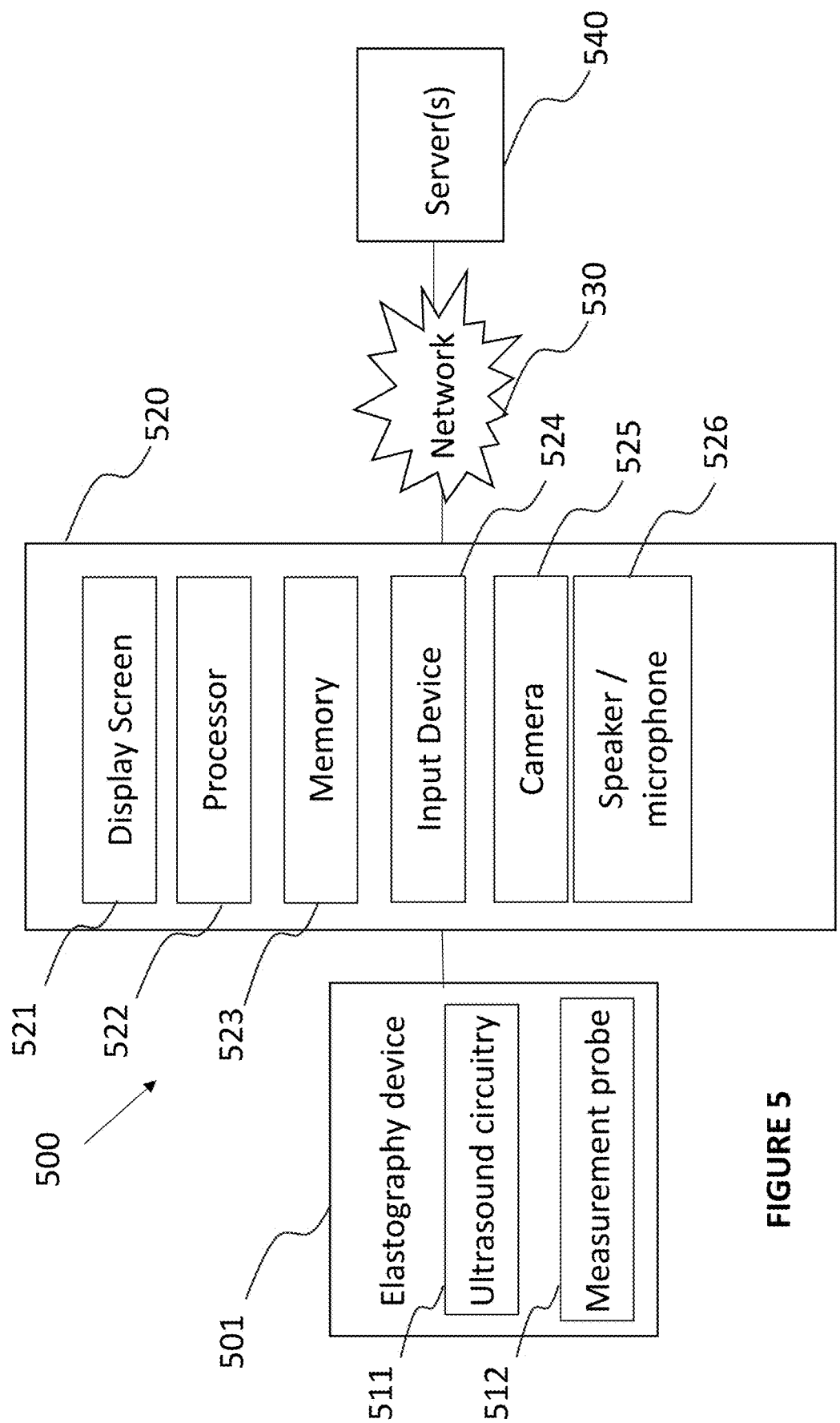
FIG. 5 schematically represents an elastography system according to an embodiment of the invention, and FIG. 6 schematically represents an elastography device according to an embodiment of the invention.

In particular, FIG. 5 illustrates a schematic block diagram of an example of an elastography system 500 upon which various aspects of the technology described herein may be practiced. The elastography system 500 includes an elastography device 501, a processing device 520, a network 530, and one or more servers 540.

The elastography device 501 includes ultrasound circuitry 511 and a measurement probe 512 for carrying out ultrasound and elastography measurements. The processing device 520 may be a portable device (e.g., a phone, a tablet, a computer or a separate medical device) that includes a display screen 521 a processor 522, a memory 523, an input device 524, a camera 525 and a speaker 526. The processing device 520 is in wired (e.g., through a lightning connector or a mini-USB connector) and/or wireless communication (e.g., using BLUETOOTH® (a short-range wireless technology standard), ZIGBEE, and/or WiFi wireless protocols) with the elastography device 501. In addition, optionally, the processing device 520 is in wireless communication with the one or more servers 540 over the network 530. However, the wireless communication with the server(s) is optional.

The elastography device 501 may be configured to generate elastography and ultrasound data that may be employed to generate an ultrasound image and an elastogram image. The elastography device 501 may be constructed in any of a variety of ways. In some embodiments, the elastography device 501 may be a vibration-controlled-transient-elastography device that is configured to perform liver stiffness measurements. An example of a vibration-controlled-transient-elastography device is shown and described in FIG. 6.

The ultrasound circuitry 511 may be configured to generate the ultrasound and elastography data. The ultrasound device 501 may transmit ultrasound data and/or ultrasound images and/or elastography data (such as, but not limited to, liver stiffness measurements) to the processing device 520 over a wired (e.g., through a lightning connector or a mini-USB connector) and/or wireless (e.g., using BLUETOOTH® (a short-range wireless technology standard), ZIGBEE, and/or WiFi wireless protocols) communication link.

Referring now to the processing device 520, the processor 522 may include specially-programmed and/or special-purpose hardware such as an application-specific integrated circuit (ASIC). For example, the processor 522 may include one or more graphics processing units (GPUs). The processing device 520 may be configured to process the ultrasound data and/or elastography data received from the elastography device 501 to generate ultrasound and/or elastogram images for display on the display screen 521. The processing device 520 may also be configured to determine the index of the cardiac function to provide an indication of a degree of congestion of the heart of the subject. In one or more embodiments, the processing device 520 receives the first and second liver stiffness measurements from the elastography device 501 to determine the index of the cardiac function.

The processing of the liver stiffness measurement to determine the index of the cardiac function may be performed by, for example, the processor 522. In one or more embodiments, the processor 522 may also be adapted to control the acquisition of ultrasound and/or elastography data with the elastography device 501. In one or more embodiments, the processor 522 may also be adapted to control the display screen 521 via a graphical user interface and/or speaker/microphone 526 to instruct and guide the operator of the elastography device 501 to carry out specific steps of the method for assessing a cardiac function of a subject. For example, the processor 522 may be configured to control the display screen 521 to display via a graphical user interface to carry out the first liver stiffness measurement. Then, the processor 522 may be configured to control the display screen 521 to display via a graphical user interface a drop-down menu to select one or more predetermined cardiac stimulations from a plurality of selectable predetermined cardiac stimulations. The selection of one or more predetermined cardiac stimulations via the graphical user interface may trigger, by the processor 522, a routine that prompts the operator of the elastography device 501 to a) perform the first liver stiffness measurement at a first time t1, b) initiate the predetermined cardiac stimulation and c) perform the second liver stiffness measurement at a second time t2. After determining the index of the cardiac function based on the received first and second liver stiffness measurement data, the processor 522 may also be adapted to control the display screen 521 to display via a graphical user interface a visual indicator indicative of the determined index of the cardiac function to provide an indication of a degree of congestion of the heart of the subject.

The processing device 520 may be configured to perform certain of the processes and methods described herein using the processor 522 (e.g., one or more computer hardware processors) and one or more articles of manufacture that include non-transitory computer-readable storage media such as the memory 523. The processor 522 may control writing data to and reading data from the memory 523 in any suitable manner. To perform certain of the processes described herein, the processor 522 may execute one or more processor-executable instructions stored in one or more non-transitory computer-readable storage media (e.g., the memory 523), which may serve as non-transitory computer-readable storage media storing processor-executable instructions for execution by the processor 522. The camera 525 may be configured to detect light (e.g., visible light) to form an image. The display screen 521 may be configured to display images and/or videos, and may be, for example, a liquid crystal display (LCD), a plasma display, and/or an organic light emitting diode (OLED) display on the processing device 520. The input device 524 may include one or more devices capable of receiving input from a user and transmitting the input to the processor 522. For example, the input device 524 may include a keyboard, a mouse, a microphone, touch-enabled sensors on the display screen 521, and/or a microphone. The display screen 521, the input device 524, the camera 525, and the speaker 540 may be communicatively coupled to the processor 522 and/or under the control of the processor 522.

It should be appreciated that the processing device 520 may be implemented in any of a variety of ways. For example, the processing device 520 may be implemented as a handheld device such as a mobile smartphone or a tablet. Thereby, a user of the elastography device 501 may be able to operate the elastography device 501 with one hand and hold the processing device 520 with another hand. In other examples, the processing device 520 may be implemented as a portable device that is not a handheld device, such as a laptop. In yet other examples, the processing device 520 may be implemented as a stationary device such as a desktop computer connected to the elastography device. The processing device 520 may be connected to the network 530 over a wired connection (e.g., via an Ethernet cable) and/or a wireless connection (e.g., over a WiFi network). The processing device 520 may thereby communicate with (e.g., transmit data to) the one or more servers 540 over the network 530. In one or more embodiments, the processing device 520 may communicate the determined index of the cardiac function to the one or more servers 540 via the network 530.

FIG. 5 should be understood to be non-limiting. For example, the elastography system 500 may include fewer or more components than shown and the processing device 520 may include fewer or more components than shown. While FIG. 5 represents an elastography system 500 in which the processing device 520 is separate from the elastography device 501, it will be appreciated that the processing device 520 can be part of (e.g. included in) the elastography device. For example, the display screen 521, the processor 522, the memory 523, the input device 524 and the speaker/microphone 526 can be elements of the elastography device 501. In this implementation, the processor 522 can be part of, or can control, or can be under the control of, the ultrasound circuitry 511 or can be controlled by a master processor of the elastography device 501.

Moreover, it will be appreciated that the processing device 520 could be in communication with more than one elastography devices so as to receive liver stiffness measurements from a plurality of elastography devices. Furthermore, it is contemplated that the first and second liver stiffness measurements could be carried out with, respectively, different elastography devices and/or with, respectively, different elastography techniques (such as VCTE and ARFI).

Referring back to the embodiments of FIG. 3 or 4, the graphical user interface 311 of the screen 310 may also display instructions to guide the procedure to the operator (for example "place the subject in a lying supine position", "trigger the first measurement", "elevate the subject's left leg", "trigger the second measurement"). The elastography device 300 or the device integrating the computing device may also comprise a speaker 340 to dictate the instructions to guide the procedure to the operator.

For example, in one or more embodiments, the display screen 310 and the graphical user interface 311 may be controlled by the computing module or processing circuit 200 or by a master processor or master control circuit of the elastography device 300 to display a drop-down menu or menu including a plurality of selectable predetermined cardiac stimulations to be performed by the subject. In one or more embodiments of the invention, each of the selectable predetermined cardiac stimulations to be performed by the subject is associated with a specific first time t1 and/or second time t2 at which the first and/or second liver stiffness measurements should be carried out. In one or more embodiments of the invention, the selection of a predetermined cardiac stimulation via the graphical user interface triggers the routine or procedure that prompts the operator of the elastography device 300 to a) perform the first liver stiffness measurement at a first time t1, b) initiate the predetermined cardiac stimulation and c) perform the second liver stiffness measurement at a first time t2. As explained above, it will be appreciated that the predetermined cardiac stimulation b) can be initiated prior to performing the first liver stiffness measurement at a first time t1 at a). In one or more embodiments of the invention, the graphical user interface is configured to display a visual indicator indicative of the determined index of the cardiac function based on the first and second measured liver stiffness values to provide an indication of a heart condition of the subject.

In the embodiments of FIG. 3 or 4, the value of the CHC index and/or the risk class may be transmitted to a separate external device, for example a medical device for monitoring vital signs.

FIG. 6 shows an exemplary embodiment of a vibration-controlled-transient-elastography device 601 that is configured to perform liver stiffness measurements. The vibration-controlled-transient-elastography device 601 may be an implementation of the elastography device 501 shown in FIG. 5 or the elastography device 300 shown in FIGS. 3 and 4.

The elastography device 601 of FIG. 6 comprises a probe 602 including a probe casing 603 (which forms the main body of the probe), to be handheld, and a protruding part, which protrudes from the casing 603. The protruding part can thus be applied against the body 608 of the subject, to deliver mechanical pulses to tissues 80, and to transmit and acquire U/S shots. In this embodiment, the protruding part is a tip 604, for instance a cylindrical tip (with a circular transducer 606 at its end).

Still, in other embodiments, the protruding part could be an ultrasound head (located at an end of the probe) including an array, for instance a linear array of U/S transducers. In this regard, it may be noted that the proposed technique can be used with a single element ultrasound transducer (like in the case of FIG. 6, which can be of various shapes: rectangular or ellipsoidal or circular for example), or with a multi-element ultrasound transducer (like an array of U/S transducers, for example a linear or convex or phased array ultrasound probe). While a single element ultrasound transducer is adapted to display A-mode and M-mode ultrasound imaging, a multi element ultrasound transducer can also display a B-mode image allowing an easier localization of the to-be-measured tissue. In the case of a multi element ultrasound transducer, at least one of the beamformed ultrasound lines is used to track how the mechanical pulses propagate. To this end, using the center beamformed ultrasound line (which is aligned with the probe axis) is beneficial, for symmetry considerations.

The probe 602 comprises also a low frequency vibrator 605, and the U/S (ultrasound) transducer 606, which is fixed at an end of a tip 604. Here, the U/S transducer 606, plays both the role of an ultrasound emitter and the role of an ultrasound receiver (alternatively). Still, in other embodiments, the probe may comprise an U/S emitter and an U/S receiver distinct from each other. Here, the U/S transducer 606 is arranged on the axis z of the vibrator. Still, in other embodiments, the U/S transducer could be located elsewhere on the probe, not necessarily on the vibrator's axis.

The tip 604 is actuated by the low frequency vibrator 605. Here, the vibrator 605 is arranged to move the tip 604 relative to the probe casing 603. The vibrator 605 is arranged to move a shaft 604', the end of which forming the tip 604 of the probe. Still, in other embodiments, the tip, or, more generally, the protruding part of the probe, could be bound to the probe casing with no motion with respect to the probe casing, the vibrator being then arranged to move a mass, inside the casing, to make the whole probe moving towards the tissue and back (by virtue of a recoil effect).

The vibrator 605 is a low frequency vibrator in that it moves the tip with a central, average frequency smaller than 500 hertz, or even smaller than 100 hertz (in contrast with ultrasound shots or echo signals, whose central frequency is typically higher than 1 megahertz, for instance between 1 and 5 megahertz). The vibrator is a low-frequency electromechanical actuator, for instance with one or several coils and magnets, similar to a loud-speaker actuator.

In this device 601, the vibrator 605 is rotationally symmetrical around a vibrator axis, which coincide with the probe axis z. When the vibrator 605 vibrates, it induces displacements that are mainly longitudinal, parallel to its axis. The shaft 604' is centered onto the axis z, and the vibrator 605 is arranged to move this shaft along the axis z.

In practice, the displacement of the ultrasound transducer 606, induced by the vibrator 605, has a peak-to-peak amplitude between 0.2 mm and 10 mm, and, in an embodiment, between 0.5 and 2 mm.

The probe 602 comprises a displacement sensor 611, arranged to output a measurement signal Sd representative of the displacement of the ultrasound transducer 606. In this embodiment, the measurement signal Sd is representative of the displacement of the ultrasound transducer 606 relative to the probe casing 603. A part of the displacement sensor 611 is fixed on the shaft mentioned above while another part of the sensor is fitted in the probe, with no motion with respect to the casing 603. The displacement sensor 611 may be a Hall-effect sensor, an induction displacement sensor, or any other suitable sensor.

The device 601 comprises also a central unit 607 comprising an electronic unit, connected to the vibrator 605 and to the U/S transducer 606. The computing module or processing circuit 200 of FIG. 3 or the processing unit 520 of FIG. 5 can be part of the central unit 607 or external to the central unit 607 (as shown in FIG. 4 or FIG. 5).

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

A person skilled in the art will readily appreciate that various parameters disclosed in the description may be modified and that various embodiments disclosed may be combined without departing from the scope of the invention. The articles "a" and "an" may be employed in connection with various elements, components, processes, steps, procedures, or structures described herein. This is merely for convenience and to give a general sense of the elements, components, processes, steps, procedures or structures. Such a description includes "one or at least one" of the elements, components, processes or structures. Moreover, as used herein, the singular articles also include a description of a plurality of elements, components, processes or structures, unless it is apparent from a specific context that the plural is excluded.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

It will be appreciated that the various embodiments and aspects of the inventions described previously are combinable according to any technically permissible combinations. For example, various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Having described above several aspects of at least one embodiment, it is to be appreciated various alterations, modifications, and improvements will readily occur to those skilled in the art. Such alterations, modifications, and improvements are intended to be aspects of this disclosure. Accordingly, the foregoing description and drawings are by way of example only.

The invention claimed is:

1. A method for determining an index for assessing a cardiac function of a subject, the method comprising:
    performing, by elastography, a first liver stiffness measurement to obtain a first value of a liver stiffness parameter of the subject, said first value being associated with a first time;
    performing, by elastography, a second liver stiffness measurement to obtain a second value of the liver stiffness parameter of the subject, said second value being associated with a second time strictly greater than the first time;
    determining, by a processing circuit, the index of the cardiac function based on the first value and the second value of the liver stiffness parameter, and
    displaying, via a graphical user interface of a display, a visual indicator associated with the determined index of the cardiac function to estimate a cardiac function of the heart of the subject,
    wherein the first value corresponds to a value of the liver stiffness parameter obtained before or immediately after carrying out a predetermined cardiac stimulation that modifies a cardiovascular system of the subject and the second value corresponds to a value of the liver stiffness parameter that is obtained after carrying out the first liver stiffness measurement and the predetermined cardiac stimulation, and
    wherein a value of a difference between the second time and the first time is at most 6 hours.

2. The method of claim 1, wherein the predetermined cardiac stimulation comprises at least one of:
    a change of position of the subject;
    a training exercise performed by the subject; and
    an injection of a substance modifying an hemodynamic property of the subject.

3. The method of claim 2, wherein the predetermined cardiac stimulation is a change of position of the subject, wherein the value of the difference between the second time and the first time is at most 15 minutes.

4. The method of claim 3, wherein the change of position is at least one of:
    a change from a standing position to a supine position or a change from a supine position to a standing position;

a change from a Trendelenburg position to a supine position or a change from a supine position to a Trendelenburg position;

a change from a supine position in which at least one leg of the subject is lowered to a supine position in which the at least one leg of the subject is elevated, or a change from a supine position in which at least one leg of the subject is elevated to a supine position in which the at least one leg of the subject is lowered, and a change from a Fowler's position to a supine position or a change from a supine position to a Fowler's position.

5. The method of claim 2, wherein the predetermined cardiac stimulation comprises a training exercise.

6. The method of claim 5, wherein the predetermined cardiac stimulation further comprises an administration of an inotropic, vasoconstricting or vasodilating substance.

7. The method of claim 2, wherein the predetermined cardiac stimulation comprises an injection of a substance modifying a hemodynamic property of the subject, said predetermined cardiac stimulation corresponding to a fluid induced predetermined cardiac stimulation or a hemodialysis.

8. The method of claim 1, wherein the index of the cardiac function is a function of a difference between the first value and the second value.

9. The method of claim 1, wherein the determining of the index is further based on the first time and the second time.

10. The method of claim 1, further comprising:

obtaining a set of at least one additional value of the liver stiffness parameter of the subject, each additional value being associated with a time comprised between the first time and the second time;

wherein the determination of the index of the cardiac function is further based on the set of at least one additional value.

11. The method of claim 10, wherein the set of at least one additional value comprises n−2 values $LSM_2, \ldots LSM_{n-1}$, n being an integer greater than or equal to 3, wherein the index is a function of:

$$\sum_{i=1}^{n} \alpha_i LSM_i$$

where $LSM_1$ designates the first value of the liver stiffness parameter, $LSM_n$ designates the second value of the liver stiffness parameter, where $\alpha_i$ are real coefficients such as:

$$\sum_{i=1}^{n} \alpha_i = 0.$$

12. The method of claim 11, further comprising selecting via the graphical user interface the predetermined cardiac stimulation from among one of a plurality of predetermined cardiac stimulations.

13. The method of claim 12, wherein the selecting via the graphical user interface automatically determines a time at which the second liver stiffness measurement is carried out.

14. The method of claim 1, wherein the display is comprised in an elastography device.

15. The method of claim 1, wherein the processing circuit is a processing circuit of a device that is external an elastography device that is configured to perform the first and second liver stiffness measurements.

16. A system for determining an index for assessing a cardiac function of a subject, said elastography system comprising:

an elastography device configured to perform liver stiffness measurements;

a processing circuit to receive liver stiffness measurement data from the elastography device, the processing circuit including a processor and a non-transitory memory coded with machine readable instructions that, when executed by the processor, determines the index of the cardiac function based on a first value of a first liver stiffness parameter measured by the elastography device at a first time and a second value of the liver stiffness parameter measured by the elastography device at a second time strictly greater than the first time, and a display including a graphical user interface that is configured to display a visual indicator associated with the determined index of the cardiac function to estimate a cardiac function of the heart of the subject, wherein the first value corresponds to a value of the liver stiffness parameter before or immediately after carrying out a predetermined cardiac stimulation that modifies a cardiovascular system of the subject and the second value corresponds to a value of the liver stiffness parameter that is obtained after carrying out the first liver stiffness measurement and the predetermined cardiac stimulation, and wherein a value of a difference between the second time and the first time is at most 6 hours.

17. The system of claim 16, wherein the processing circuit is further configured to determine a heart condition based on the determined index and on at least one threshold.

18. The system of claim 17, wherein the processing circuit is further configured to obtain at least one information relative to:

a fibrosis parameter of the subject;

a biological parameter of the subject, and an anthropometric parameter of the subject, and wherein the processing circuit is configured to determine the at least one threshold and/or the heart condition based on the obtained information.

19. The system of claim 16, wherein the elastography device comprises the processing circuit and the graphical user interface.

20. The system of claim 16, wherein the display including the graphical user interface is configured to display a plurality of selectable predetermined cardiac stimulations.

\* \* \* \* \*